US010842101B2

(12) United States Patent
Kang et al.

(10) Patent No.: US 10,842,101 B2
(45) Date of Patent: Nov. 24, 2020

(54) WHEAT CULTIVAR OFREE FOR IMPROVEMENT OF GLUTEN INTOLERANCE AND WHEAT-DEPENDENT EXERCISE-INDUCED ANAPHYLAXIS

(71) Applicants: Republic of Korea (Management: Rural Development Administration), Jeonju-si (KR); Industrial Cooperation Foundation Chonbuk National University, Jeonju-si (KR)

(72) Inventors: Chon Sik Kang, Jeonju-si (KR); Jong-Yeol Lee, Suwon-si (KR); Chul Soo Park, Jeonju-si (KR); Young Keun Cheong, Iksan-si (KR); Kyeong Hoon Kim, Miryang-si (KR); Jae Han Son, Wanju-Gun (KR); Jong Chul Park, Jeonju-si (KR); Kwang Geun Park, Hwaseong-si (KR); Ki Hun Park, Jeonju-si (KR); Young-Mi Kim, Suwon-si Gyeonggi-do (KR); Sun-Hyung Lim, Jeonju-si (KR); Bo Kyeong Kim, Iksan-si (KR)

(73) Assignees: REPUBLIC OF KOREA (MANAGEMENT: RURAL DEVELOPMENT ADMINISTRATION), Jeonju-si (KR); INDUSTRIAL COOPERATION FOUNDATION CHONBUK NATIONAL UNIVERSITY, Jeonju-si (KR)

( * ) Notice: Subject to any disclaimer, the term of this patent is extended or adjusted under 35 U.S.C. 154(b) by 141 days.

(21) Appl. No.: 15/752,992

(22) PCT Filed: Jun. 16, 2017

(86) PCT No.: PCT/KR2017/006335
§ 371 (c)(1),
(2) Date: Feb. 15, 2018

(87) PCT Pub. No.: WO2017/217812
PCT Pub. Date: Dec. 21, 2017

(65) Prior Publication Data
US 2018/0352778 A1    Dec. 13, 2018

(30) Foreign Application Priority Data

Jun. 17, 2016 (KR) .................. 10-2016-0075793
Jun. 15, 2017 (KR) .................. 10-2017-0076010

(51) Int. Cl.
*A01H 6/46* (2018.01)
*A01H 5/10* (2018.01)
*A21D 13/06* (2017.01)
*A21D 13/066* (2017.01)

(52) U.S. Cl.
CPC .............. *A01H 6/4678* (2018.05); *A01H 5/10* (2013.01); *A21D 13/066* (2013.01)

(58) Field of Classification Search
None
See application file for complete search history.

(56) References Cited

U.S. PATENT DOCUMENTS

| 2015/0182607 A1 | 7/2015 | Jolly et al. |
| 2015/0272171 A1 | 10/2015 | Lamacchia et al. |

FOREIGN PATENT DOCUMENTS

| JP | 2010098984 A | 5/2010 |
| KR | 20150063535 A | 6/2015 |
| WO | 2009035651 A1 | 3/2009 |

OTHER PUBLICATIONS

Lee et al. Mapping of QTL for yield and its related traits in a doubled haploid population of Korean wheat. (2014) Plant Biotechnol. Rep.; vol. 8; pp. 443-454 (Year: 2014).*
Lee et al. Characterization of a wheat mutant missing low-molecular weight glutenin subunits encoded by the B-genome. (2017) Journal of Cereal Science; vol. 73; pp. 158-164 (Year: 2017).*
Ahn et al. Effect of allelic variations at the Glu-D1, Glu-A3, Glu-B3 and Pinb-D1 loci on flour characteristics and bread loaf volume. (2014) International Food Research Journal; vol. 21; pp. 1141-1149 (Year: 2014).*
Van den Broeck et al. Removing celiac disease-related gluten proteins from bread wheat while retaining technological properties: a study with Chinese Spring deletion lines. (2009) BMC Plant Biology; vol. 9; pp. 1-12 (Year: 2009).*
Yamauchi et al. The bread-making quality of a domestic flour blended with an extra strong flour, and staling of the bread made from the blended flour. (2001) Food Science and Technology Research; vol. 7; abstract only; pp. 1-4 (Year: 2001).*
Extended European Search Report dated Oct. 2, 2019 in EP Application No. 17813635.4.
Van Den Broeck et al., "Removing celiac disease-related gluten proteins from bread wheat while retaining technological properties: a study with Chinese Spring deletion lines," BMC Plant Biology, vol. 9, No. 41, pp. 1-12 (2009).

(Continued)

*Primary Examiner* — Cathy Kingdon Worley
(74) *Attorney, Agent, or Firm* — Panitch Schwarze Belisario & Nadel LLP

(57) ABSTRACT

The present invention relates to Ofree, a novel wheat cultivar produced by crossing Keumkang wheat and Olgeuru wheat, in which low-molecular-weight glutenin subunit (LMW-GS) alleles located at the Glu-B3 loci (major cause of gluten intolerance) and ω-5 gliadin genes (major cause of wheat-dependent exercise-induced anaphylaxis (WDEIA)) have been deleted; a method of developing a new wheat cultivar using Ofree; wheat flour produced from Ofree; a method of producing a processed food using the wheat flour; and a processed food produced by the aforementioned production method. It is expected that Ofree provided in the present invention can be widely used for the production of processed foods capable of preventing the onset of celiac disease caused by gluten intolerance and the onset of WDEIA.

10 Claims, 10 Drawing Sheets

Specification includes a Sequence Listing.

(56) References Cited

OTHER PUBLICATIONS

Van Herpen, T., "Coeliac Disease Safe Gluten," 188 pages (2008).
Lee et al, "Low-Molecular-Weight Glutenin Subunits in Common Wheat (*Triticum aestivum* L.)," Korean Journal of Breeding Science, vol. 46, No. 4, pp. 342-352 (Dec. 2014).
Si et al., "Cloning and Charcterization of Low-Molecular-Weight Glutenin Subunit Alleles from Chinese Wheat Landraces (*Triticum aestivum* L.)," The Scientific World Journal, vol. 2014, pp. 1-6 (Apr. 10, 2014).
Int'l Search Report dated Sep. 29, 2017 in Int'l Application No. PCT/KR2017/006335.
Lee et al., "Characterization of a Wheat Mutant Missing Low-Molecular-Weight Glutenin Subunits Encoded by the B-Genome," Journal of Cereal Science, vol. 73, pp. 158-164 (2017).

\* cited by examiner

[FIG. 1]
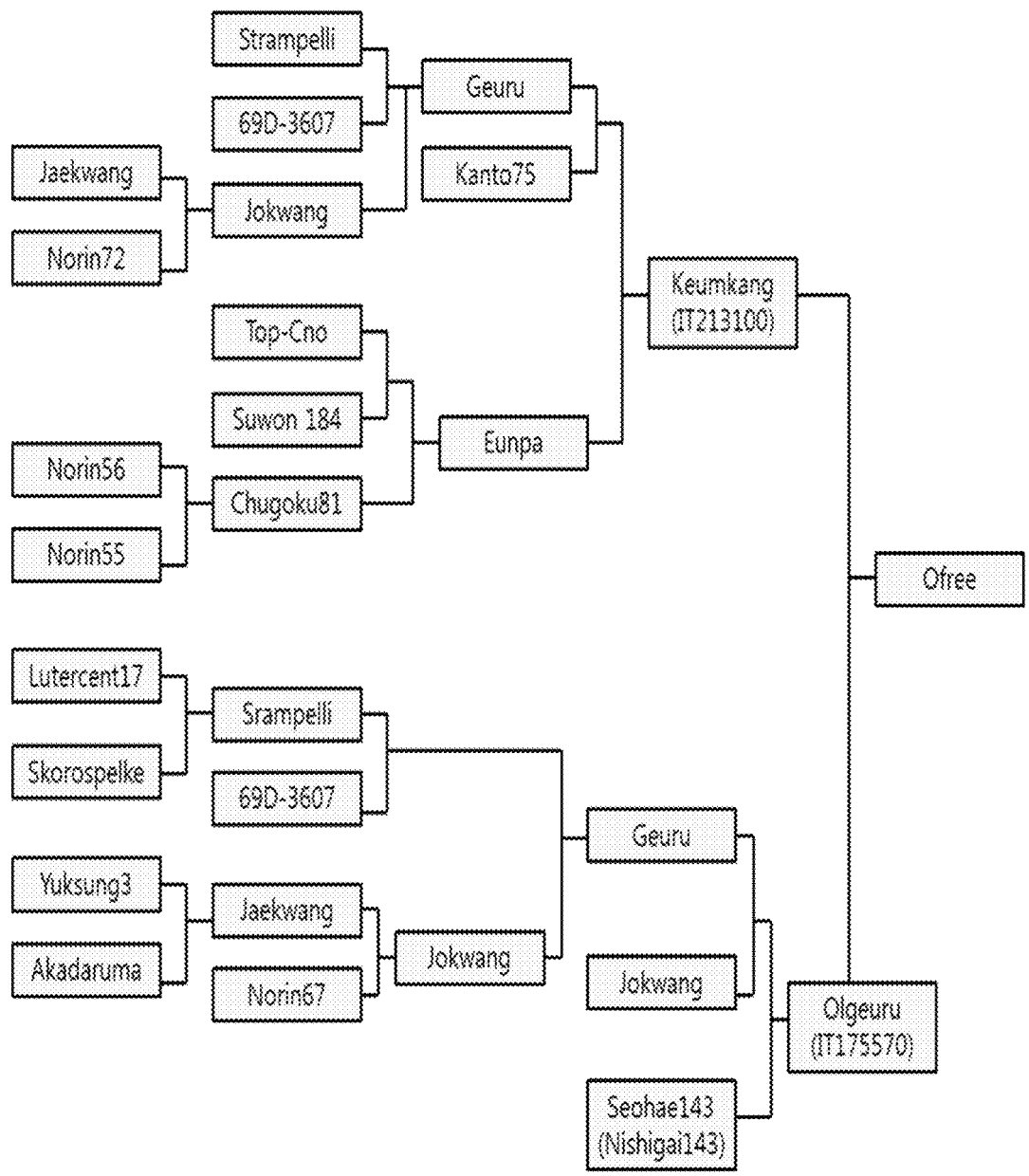

[FIG. 2A]
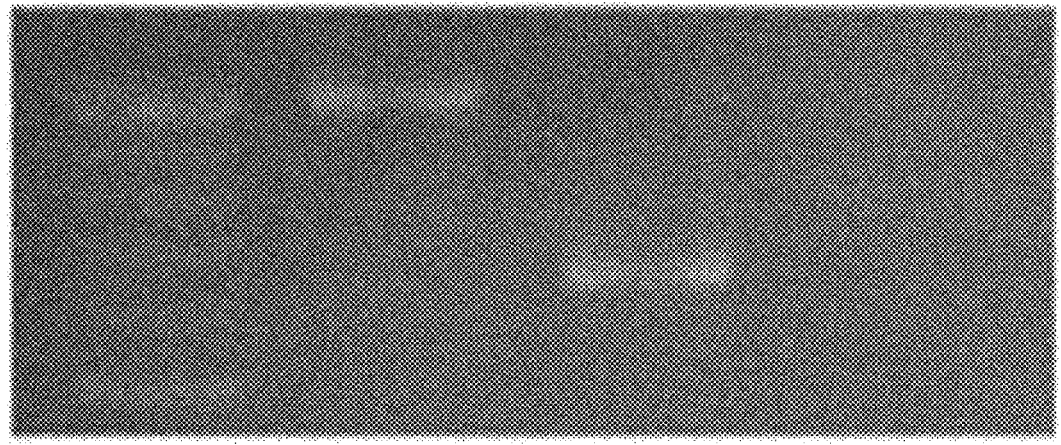

[FIG. 2B]
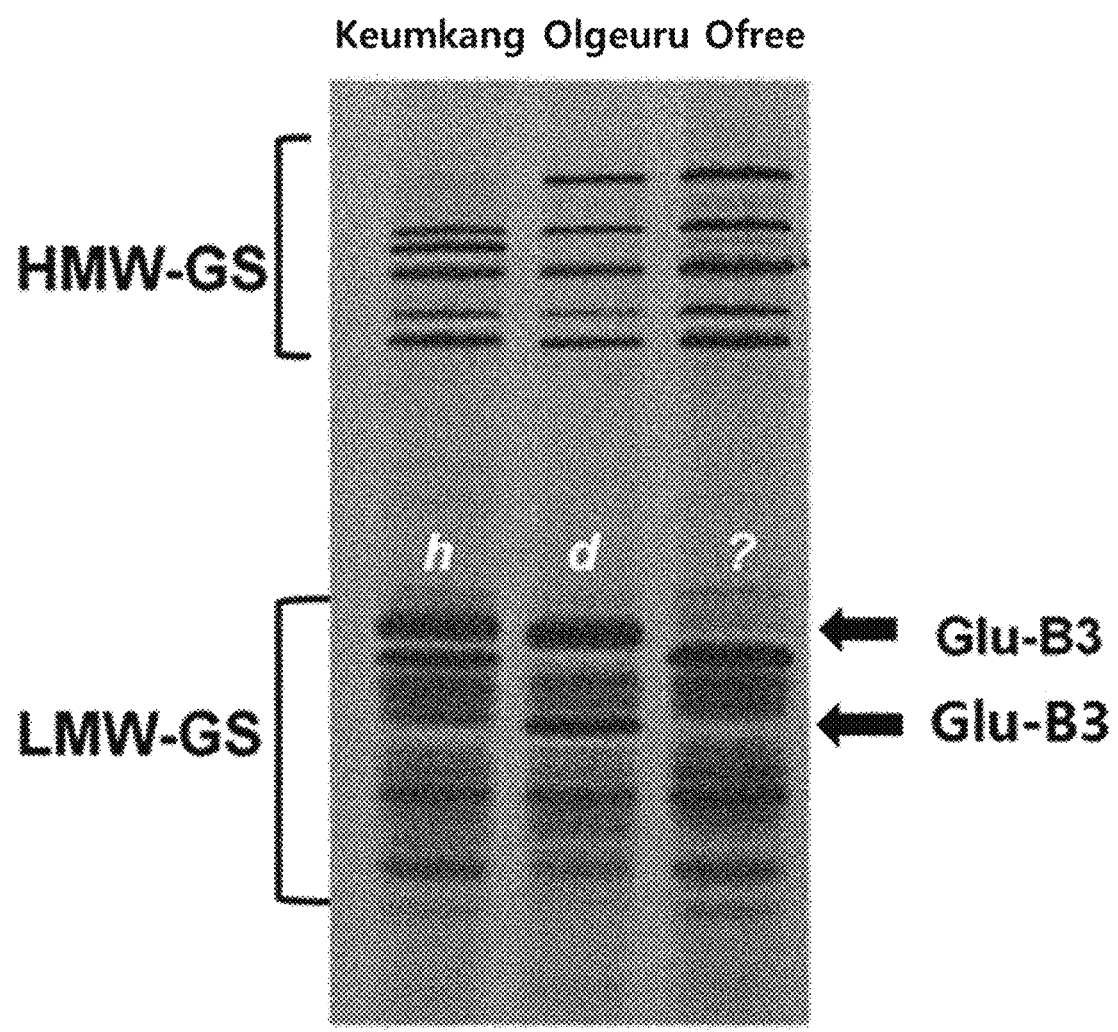

[FIG. 2C]
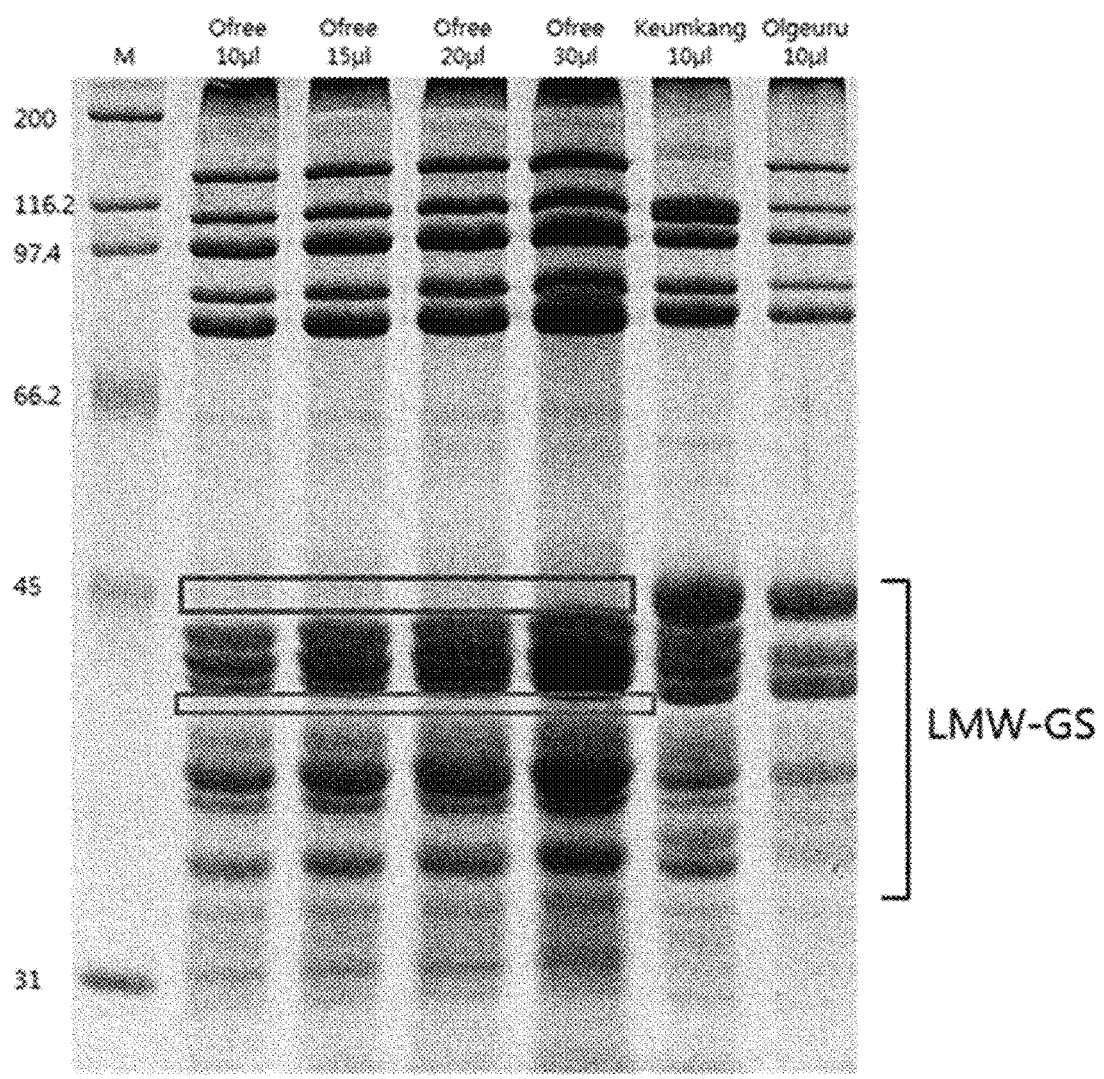

[FIG. 3]
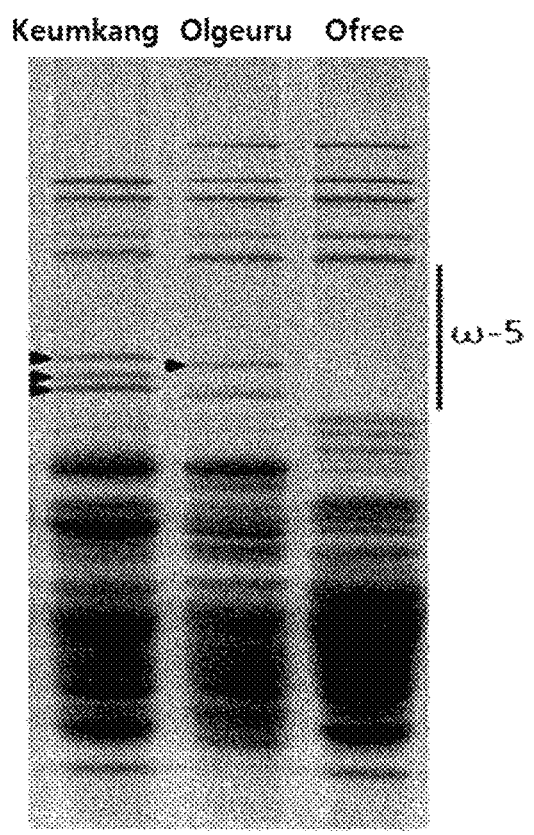

[FIG. 4]
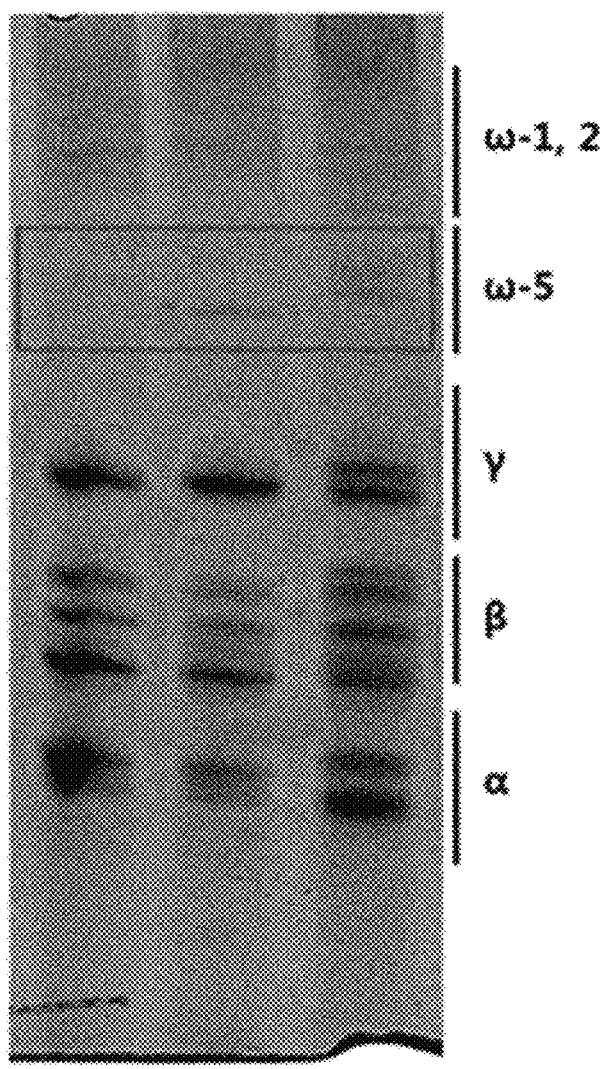

[FIG. 5]
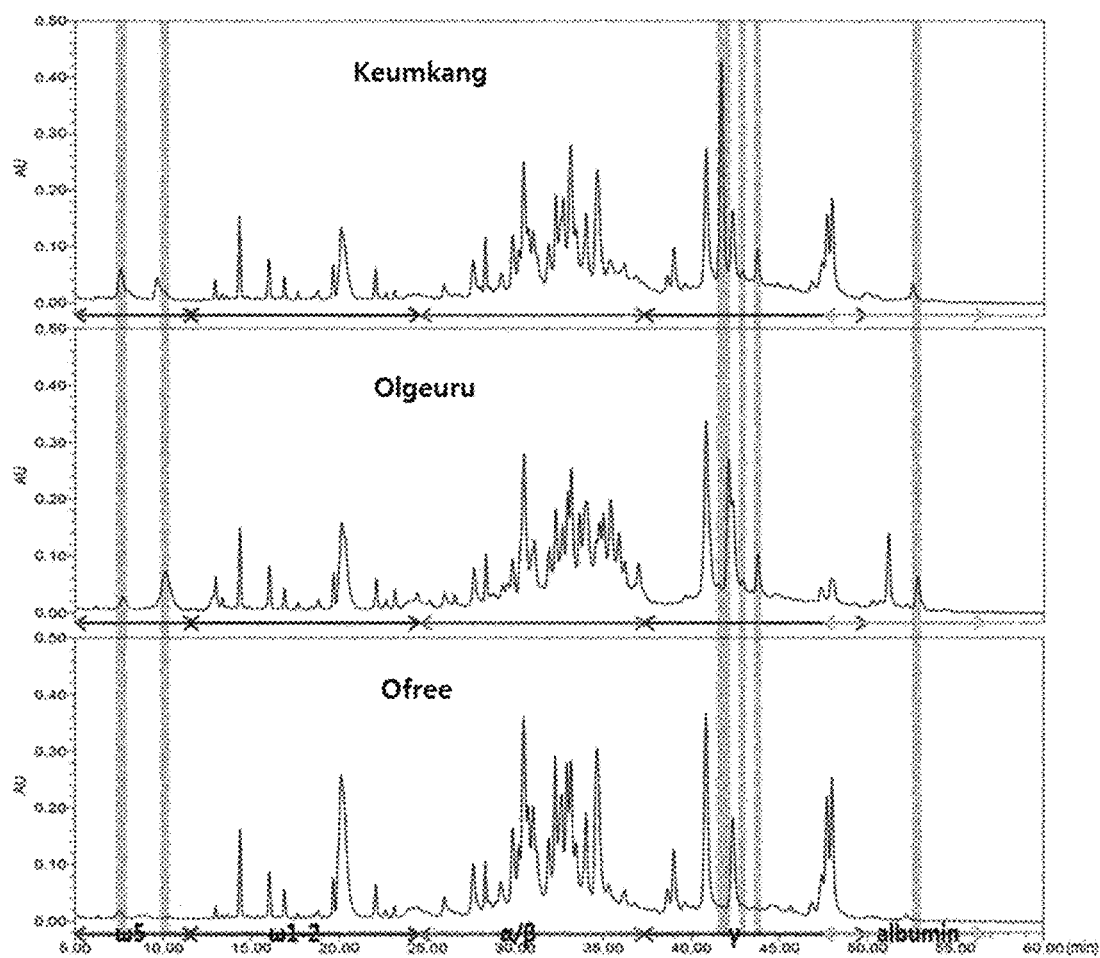

[FIG. 6]
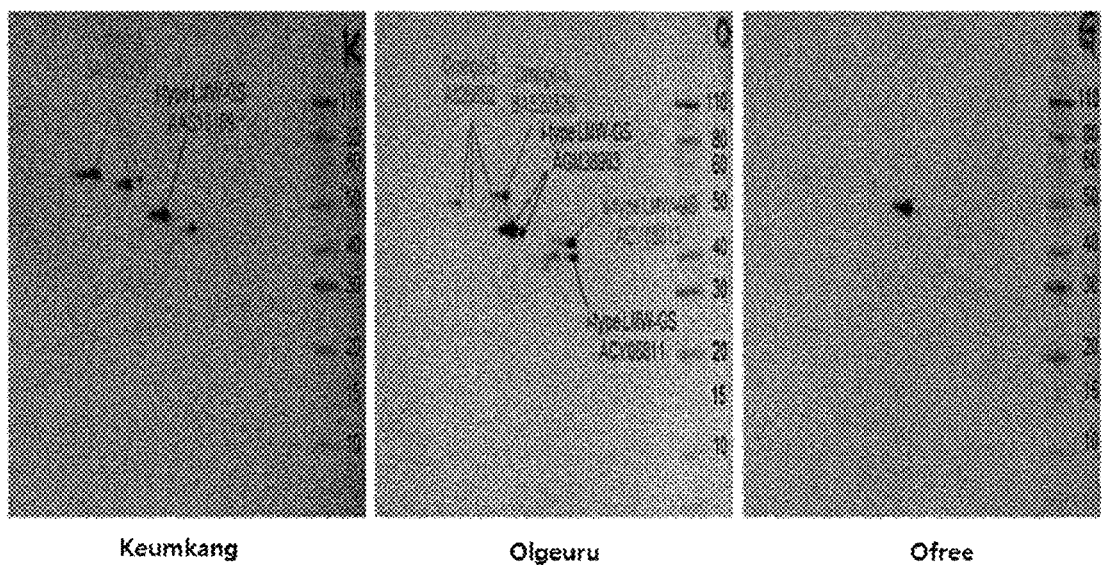

[FIG. 7]
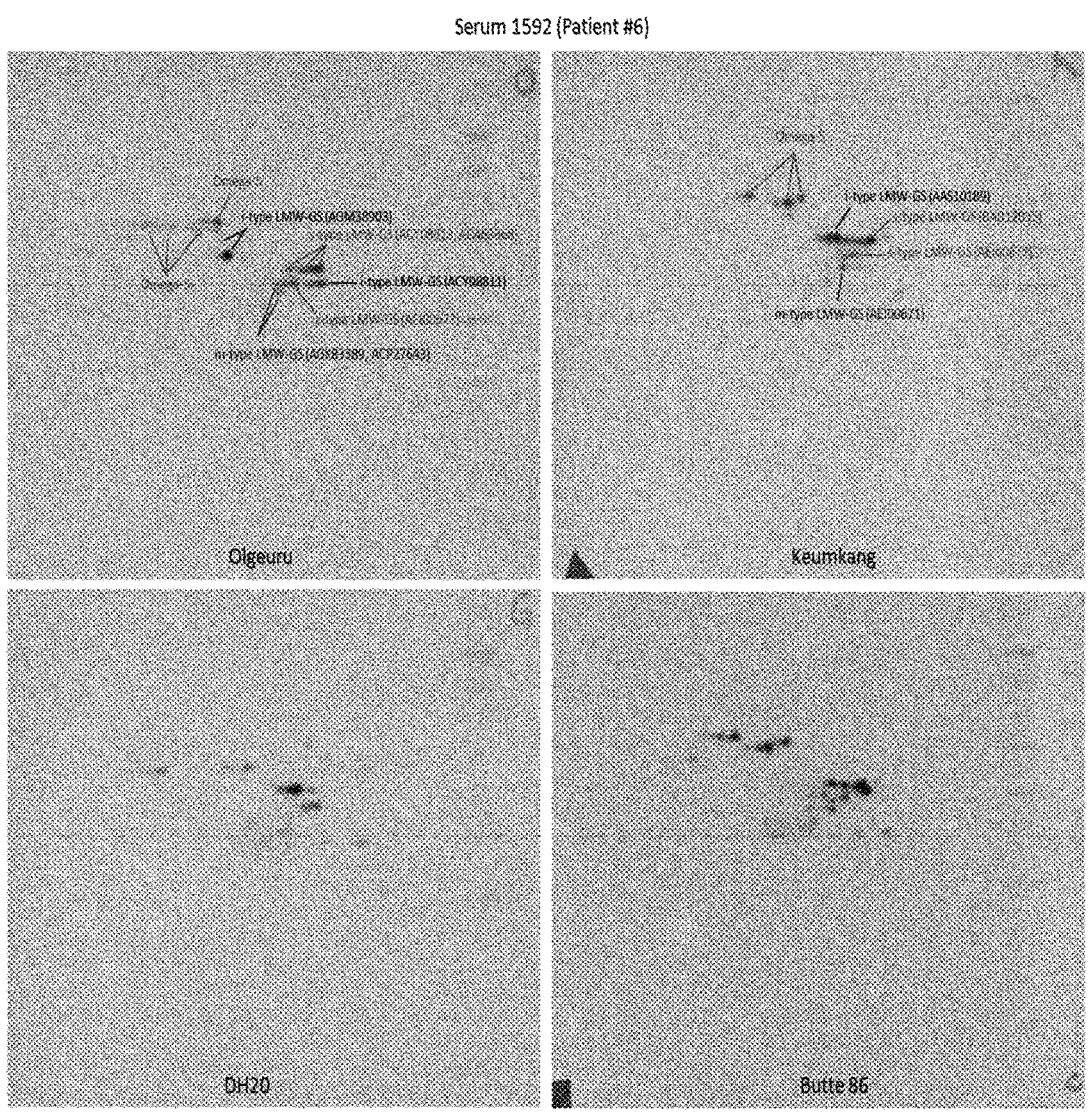

[FIG. 8]
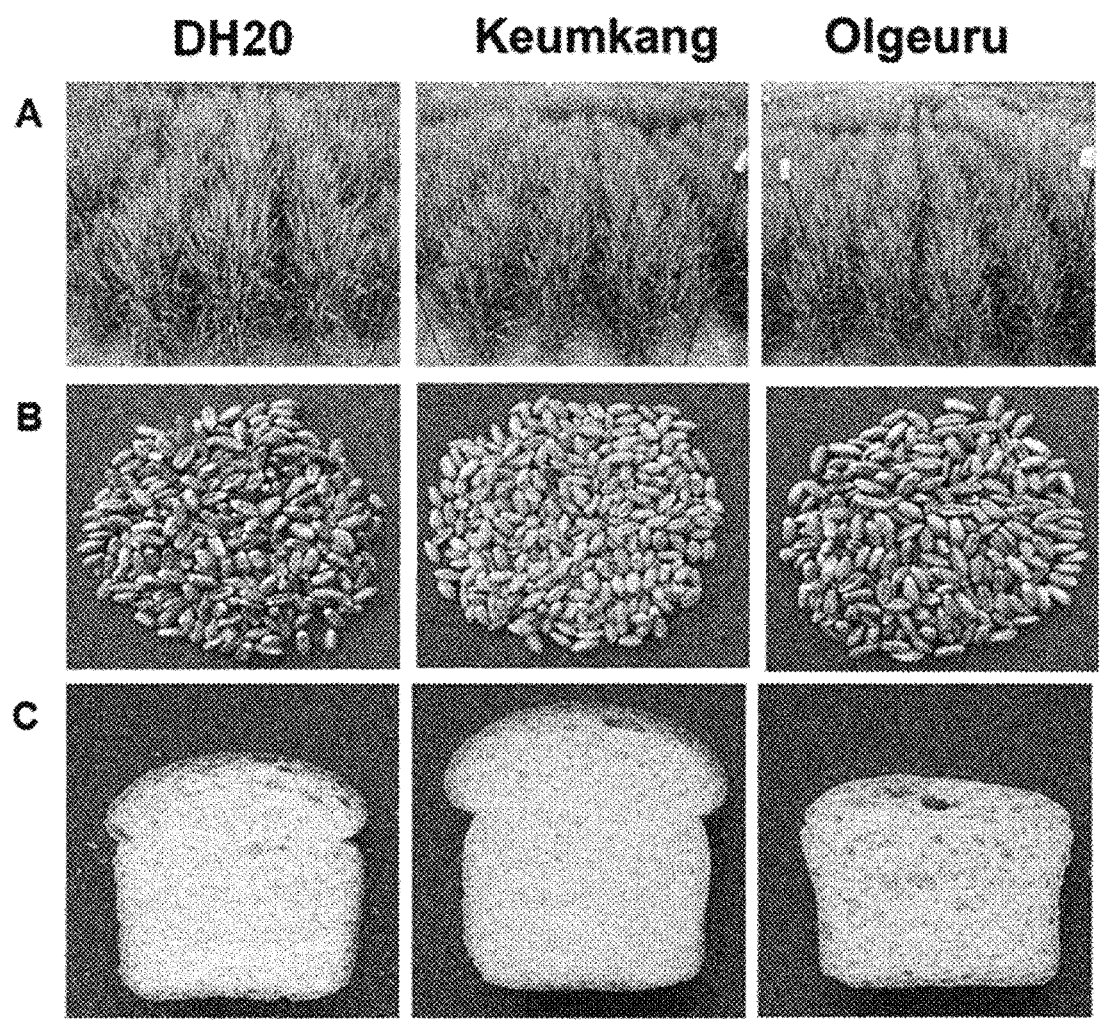

WHEAT CULTIVAR OFREE FOR IMPROVEMENT OF GLUTEN INTOLERANCE AND WHEAT-DEPENDENT EXERCISE-INDUCED ANAPHYLAXIS

CROSS-REFERENCE TO RELATED APPLICATION

This application is a Section 371 of International Application No. PCT/KR2017/006335, filed Jun. 16, 2016, which was published in the Korean language on Dec. 21, 2017 under International Publication No. WO 2017/217812 A1, which claims priority under 35 U.S.C. § 119(b) to Korean Application No. 10-2016-0075793, filed Jun. 17, 2016 and Korean Application No. 10-2017-0076010, filed Jun. 15, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688588_19US", creation date of Feb. 15, 2018, and having a size of 7.2 KB. The sequence listing submitted via EFS-Web is part of the specification and is herein incorporated by reference in its entirety.

BACKGROUND

1. Field of the Invention

The present invention relates to a novel wheat cultivar for the improvement or prevention of gluten intolerance and wheat-dependent exercise-induced anaphylaxis (WDEIA) and uses thereof.

2. Discussion of Related Art

Celiac disease is a disease caused by gluten intolerance, which is a digestive disorder characterized by a difficulty in digesting gluten components contained in grains such as wheat, barley, rye, and oat, and affects the intestines among digestive organs. Unlike most people who have no problem in digesting and absorbing gluten, people having problems with gluten digestion experience an immune response induced in the gastrointestinal tract that causes inflammation in the mucosal cells of digestive organs and damages villi. In this case, nutrients cannot be easily absorbed and it caused various symptoms such as growth retardation, loss of appetite, chronic diarrhea, abdominal swelling, dermatitis herpetiformis, and anemia due to iron deficiency appear, leading to poor absorption of nutrients and eventually serious illness. That is, when ingested by a person who inherently lacks a gluten-degrading enzyme, gluten is absorbed into the intestines without being broken down, in which case the intestinal function is impaired and the villi in the mucous membrane become weak and damaged, resulting in malabsorption that may lead to an allergic reaction or hormonal disturbance.

Gluten, which is the cause of celiac disease as described, is known as a protein consisting of a gliadin, a monomer molecule, and a glutenin, a complex polymer. Glutenin consists of a high-molecular-weight glutenin subunit (HMW-GS) and a low-molecular-weight glutenin subunit (LMW-GS) that are linked to each other by a disulfide bond.

Gluten is generally known to exhibit properties necessary for the production of wheat products by containing a gliadin responsible for the viscosity found in doughs and a glutenin imparting elasticity and toughness to doughs.

Gliadin is a major constituent component of wheat gluten, accounting for 40 to 50% of total storage proteins. Gliadin exists mostly as a monomer and is classified into four groups, ω-5-, ω-1,2-, α-/β-, and γ-gliadins, based on the mobility in low-pH acid polyacrylamide gel electrophoresis (acid-PAGE or A-PAGE) or sodium dodecyl sulfate polyacrylamide gel electrophoresis (SDS-PAGE), and has a molecular weight of about 30 to 75 kDa. The γ- and ω-gliadins are present in the short arm of chromosome 1 and encoded by genes located at the Gli-A1, Gli-B1, and Gli-D1 loci and the α-/β-gliadins are present in the short arm of chromosome 6 and are encoded by genes located at the Gli-A2, Gli-B2 and Gli-D2 loci. Among all types of gliadin proteins, the α-/β- and γ-gliadins are classified as major proteins, accounting for 28 to 33% and 23 to 31%. The ω-gliadins are present in much smaller amounts, with ω-1,2 gliadins accounting for 4 to 7% and ω-5 gliadins accounting for 3 to 6%, respectively.

The ω-5 gliadin is known to be a major antigen of wheat-dependent exercise-induced anaphylaxis (WDEIA). It is a severe food allergy that leads to death in severe cases.

As the number of wheat-allergic patients has increased and the gluten-free market has expanded in Korea, attempts have been made to find a hypoallergenic wheat line having no ω-5 gliadin, ω-1,2 gliadin and α-/β-gliadin, or γ-gliadin, which are major causes of wheat allergy or celiac disease, our research team has identified and investigated some wheat lines having no gluten proteins.

Although there has been much progress in research on the loci for high-molecular-weight and low-molecular-weight glutenins and effects thereof on wheat quality until now, gliadins have been studied to a limited extent, except for in terms of some allergic reactions and basic properties, due to the complexity and difficulty of research compared to the glutenins.

Hence, the inventors of the present invention have continued research on wheat cultivars for reducing risks of a gluten allergy and a wheat allergy, and developed a wheat cultivar in which all ω-5 gliadin (major antigen of WDEIA) genes and all LMW-GS alleles located at the Glu-B3 loci (major cause of gluten intolerance) have been deleted, and thereby completed the present invention.

(Non-patent Document) Matsuo H, Morita E, Tatham A S, Morimoto K, Horikawa T, Osuna H, Ikezawa Z, Kaneko S, Kohno K, Dekio S. 2004. Identification of the IgE-binding epitope in ω-5 gliadin, a major allergen in wheat-dependent exercise-induced anaphylaxis. J Biol Chem 279: 12135-12140.

SUMMARY OF THE INVENTION

One objective of the present invention is to provide a novel wheat cultivar in which genes responsible for gluten intolerance and/or wheat-dependent exercise-induced anaphylaxis (WDEIA) have been deleted.

Another objective of the present invention is to provide a method for developing an improved wheat cultivar, the method including a process of using the aforementioned wheat cultivar as a father plant or a mother plant for crossing with another wheat cultivar.

Still another objective of the present invention is to provide wheat flour produced from the aforementioned wheat cultivar.

Yet another objective of the present invention is to provide a method for producing a processed food, the method including a process of processing the aforementioned wheat flour.

An additional objective of the present invention is to provide a processed food produced by the aforementioned method.

The inventors of the present invention have carried out various studies to develop a method for eliminating the cause of celiac disease and WDEIA by damaging glutenins and gliadins more effectively. A novel wheat cultivar in which all low-molecular-weight glutenin subunit (LMW-GS) alleles located at the Glu-B3 loci (major cause of gluten intolerance) and all ω-5 gliadin genes (cause of WDEIA) have been deleted were developed by crossing Keumkang wheat and Olgeuru. The novel wheat cultivar is distinguished genetically from Keumkang and Olgeuru in that LMW-GS alleles located at the Glu-B3 loci and/or ω-5 gliadin genes have been deleted, but it has been found to have intrinsic characteristics, agricultural traits, yield characteristics, disease resistance and baking-related quality characteristics similar to those of Keumkang or Olgeuru or intermediate between those of Keumkang and Olgeuru.

The inventors of the present invention named the novel wheat cultivar "Ofree" and deposited it with Korean Agricultural Culture Collection (KACC) of the National Institute of Agricultural Sciences (166, Nongsaengmyeong-ro, Iseomyeon, Wanju-gun, Jeollabuk-do, Republic of Korea) on Sep. 21, 2015 with the deposit number KACC88001BP. There has been no development or report of a wheat cultivar in which all LMW-GS alleles located at the Glu-B3 loci and/or all ω-5 gliadin genes have been deleted until now other than Ofree provided in the present invention. Ofree developed by the inventors of the present invention is the first of such a wheat cultivar.

To achieve the above-described objectives, one aspect of the present invention provides a novel wheat cultivar in which LMW-GS alleles located at the Glu-B3 loci and/or ω-5 gliadin genes have been deleted, which was deposited with the deposition number KACC88001BP.

The term "low-molecular-weight glutenin subunit (LMW-GS)" used herein refers to a component having a relatively low molecular weight of 36 to 44 kDa among all glutenin-constituent components. The genes encoding LMW-GSs are Glu-A3, Glu-B3 and Glu-D3 genes located at the Glu-3 loci on chromosome 1 of wheat, and the genes can be subdivided into several alleles, the combination thereof can produce various characteristics of wheat flour.

The term "glutenin" used herein refers to a protein consisting of 18 amino acids has the form of a spherical protein that has a ball shape due to the bridge formation caused by the interaction between side chains, and is a type of glutenin which is a relatively simple protein present in various grains including wheat. Glutenin consists of a high-molecular-weight glutenin subunit (HMW-GS) having a size of 96 to 136 kDa and one of the above-described LMW-GSs linked to each other by a disulfide bond, and the combination of three kinds of HMW-GSs (Glu-A1, Glu-B1 and Glu-D1) and three kinds of LMW-GSs (Glu-A3, Glu-B3 and Glu-D3) can produce various forms of glutenins.

The term "gliadin" used herein refers to a major component of wheat gluten, accounting for 40 to 50% of total storage proteins. Gliadin exists mostly as a monomer, is classified into four groups, ω-5-, ω-1,2-, α-/β- and γ-gliadins, based on the mobility in low-pH acid-PAGE (A-PAGE) or SDS-PAGE, and has a molecular weight of about 30 to 75 kDa. The γ- and ω-gliadins are present in the short arm of chromosome 1 and encoded by genes located at the Gli-A1, Gli-B1 and Gli-D1 loci, and the α-/β-gliadins are present in the short arm of chromosome 6 and encoded by genes located at the Gli-A2, Gli-B2 and Gli-D2 loci. Among all types of gliadin proteins, α-/β- and γ-gliadins are classified as major proteins, accounting for 28 to 33% and 23 to 31%, respectively. The w-gliadins are present in much smaller amounts with ω-1,2 gliadin accounting for 4 to 7% and ω-5 gliadin accounting for 3 to 6%, respectively.

The ω-5 gliadin is known to be a major antigen of WDEIA which is a severe food allergy.

The term "wheat-dependent exercise-induced anaphylaxis (WDEIA)" refers to an allergic reaction that occurs when a person having ingested food containing wheat performs physical exercise and is known to occur mainly in adults. ω-5 gliadin is known as a predominant epitope binding with the serum immunoglobulin E (IgE) of patients with WDEIA.

The novel wheat cultivar provided in the present invention, Ofree, is free of ω-5 gliadin which is a major antigen of WDEIA, and thus can improve and/or prevent WDEIA.

The term "prevent" used herein refers to any activity of inhibiting or delaying gluten intolerance and WDEIA performed as a result of ingesting the aforementioned wheat cultivar named Ofree. Ofree provided in the present invention is free of genes located at the Glu-B3 loci (responsible for gluten intolerance) and ω-5 gliadins (antigen inducing WDEIA), which means that Ofree does not have any causative substance of allergy; therefore, Ofree can prevent WDEIA and celiac disease caused by gluten intolerance.

The term "improve" used herein encompasses activities intended to alleviate the severity of gluten intolerance and WDEIA. Specifically, it may encompass alleviating the severity of celiac disease and WDEIA that have already occurred.

The inventors of the present invention have developed a novel wheat cultivar in which LMW-GS alleles located at the Glu-B3 loci (main cause of gluten intolerance) and/or ω-5 gliadin genes (cause of WDEIA) have been deleted by crossing Keumkang and Olgeuru, named the wheat cultivar "Ofree" and deposited the same with KACC on Sep. 21, 2015, with the deposit number KACC88001BP. In the present invention, expressions such as "Ofree wheat", "Ofree" and "novel wheat cultivar" can be interpreted to represent substantially the same wheat cultivar.

The novel wheat cultivar provided in the present invention exhibits characteristics similar to those of Keumkang or Olgeuru which are the parent wheat plants or intermediate between those of Keumkang and Olgeuru. For example, the characteristics of Ofree were found to be the same or similar to those of Olgeuru in terms of a leaf color, stem length, disease resistance, and the same or similar to those of Keumkang in terms of growth habit and panicle length. However, Ofree was found to have baking-related quality characteristics such as a flour milling percentage, ash content, flour color, protein content, gluten content, sedimentation value, dough characteristics, bread loaf volume and crumb firmness that are intermediate between those of Keumkang and Olgeuru. The yield characteristics of Ofree thereof were lower than those of Keumkang or Olgeuru, and the thousand-grain-weight thereof was higher than those of Keumkang or Olgeuru.

In one embodiment of the present invention, a novel wheat cultivar named Ofree and having high cold resistance and desirable growth habit were developed by crossing Keumkang and Olgeuru (FIG. 1), and the genetic characteristics of Ofree were analyzed. The results showed that, in Ofree, LMW-GS alleles located at the Glu-B3 loci (major cause of gluten intolerance) and ω-5 gliadin genes (cause of WDEIA) have been deleted and thus were not expressed (Table 1, FIGS. 2A to 2C and 3 to 7).

Also, the intrinsic characteristics such as stand establishment, cold resistance, growth level, leaf color, growth habit, branches and leaves and uniformity of Ofree were determined. The results showed that Ofree had generally similar intrinsic characteristics to those of Keumkang and Olgeuru except for the leaf color which was similar to that of Olgeuru and the growth habit which was similar to that of Keumkang (Table 2).

Next, the agricultural traits such as a heading date, maturing date, stem length and panicle length of Ofree were determined and the results showed that the heading date and maturing date of Ofree were generally similar to those of Keumkang and Olgeuru and the stem length of Ofree was the same as that of Olgeuru and the panicle length of Ofree was similar to that of Keumkang (Table 3).

Next, the yield characteristics, such as the number of spikes per area, number of grains per spike, thousand-grain-weight, grain weight per liter and yield per area of Ofree were determined and the results showed that Ofree had a more desirable yield quality compared to Keumkang or Olgeuru in some aspects by having a larger thousand-grain-weight compared to Keumkang or Olgeuru and an intermediate grain weight per liter between Keumkang and Olgeuru despite having a significantly lower yield per area compared to Keumkang or Olgeuru (Table 4).

In addition, the resistance of Ofree to *Fusarium* head blight, virus infection, wheat flour mildew and sheath eyespot was evaluated and the results showed that Ofree had the same level of disease resistance as Olgeuru (Table 5).

Finally, the baking-related quality characteristics of Ofree were determined. The wheat flour made from Ofree (i.e. Ofree flour) had flour milling percentage, ash content and flour color that are roughly intermediate between those of the Keumkang flour and Olgeuru flour but more similar to those of the Keumkang flour than to those of the Olgeuru flour (Table 6). Also, the Ofree flour had a protein content, gluten content, sedimentation value and dough characteristics that are roughly intermediate between those of the Keumkang flour and Olgeuru flour but more similar to those of the Keumkang flour than to those of the Olgeuru flour (Table 7). The bread produced using the Ofree flour (i.e. Ofree bread) was rated as having a larger volume and greater softness compared to the Olgeuru bread by having a bread loaf volume and crumb firmness that are intermediate between those of Keumkang bread and Olgeuru bread (Table 8).

Another aspect of the present invention provides a method for developing an improved wheat cultivar capable of improving or preventing gluten intolerance and/or WDEIA and the method including a process of using Ofree as a father plant or a mother plant for crossing with another wheat cultivar.

Ofree provided in the present invention is a wheat cultivar in which LMW-GS alleles located at the Glu-B3 loci (major cause of gluten intolerance) and/or ω-5 gliadin genes (cause of WDEIA) have been deleted. Therefore, when Ofree is used as a father plant or a mother plant for crossing with another wheat cultivar, a wheat cultivar in which genes besides the LMW-GS alleles located at the Glu-B3 loci and ω-5 gliadin genes are also deleted may be developed and such a wheat cultivar may be able to prevent gluten intolerance and WDEIA more effectively than Ofree does. In this case, the other wheat cultivar to be crossed with Ofree is not limited to a particular wheat cultivar and is, for example, Jokyung, Jopoom, Baekjoong or Goso.

Therefore, Ofree provided in the present invention may be used for the development of a new wheat cultivar capable of preventing gluten intolerance and WDEIA more effectively.

Other aspects of the present invention provide wheat flour produced from the aforementioned wheat cultivar, a method for producing a processed food, the method including a process of processing the wheat flour, and a processed food produced by the method.

The novel wheat cultivar, Ofree, provided in the present invention can prevent gluten intolerance and/or WDEIA because LMW-GS alleles located at the Glu-B3 loci and ω-5 gliadin genes therein have been deleted. Therefore, wheat flour produced from Ofree may be used as a raw material for a processed food capable of preventing the risks of gluten intolerance and WDEIA, and the processed food produced using the wheat flour may be used as a functional food for preventing the risks of gluten intolerance and WDEIA.

Specifically, the method for producing a processed food capable of preventing the risks of gluten intolerance and/or WDEIA according to the present invention includes the processes of (a) milling the novel wheat cultivar to produce wheat flour; (b) preparing a dough containing the wheat flour; and (c) processing the dough.

In the method for producing a processed food, the wheat flour described in the process (a) may be produced either from the novel wheat cultivar alone or from a mixture of the novel wheat cultivar and another wheat cultivar. Since the wheat flour produced from the novel wheat cultivar according to the present invention cannot exhibit material properties sufficient to produce any type of processed food when used alone, it may be used in combination with wheat flour produced from another wheat cultivar so as to provide properties suitable for the production of processed foods.

The amount of the wheat flour produced from the novel wheat cultivar to be mixed with the wheat flour produced from another wheat cultivar is not particularly limited as long as it is an amount sufficient to prevent the onset of gluten intolerance, celiac disease and WDEIA. For example, the wheat flour produced from the novel wheat cultivar is included at 50 to 99% v/v with respect to the entire wheat flour mixture. In other alternative examples, the wheat flour produced from the novel wheat cultivar is included at 60 to 80% v/v or 65 to 70% v/v with respect to the entire wheat flour mixture. In addition, the other wheat cultivar to be included in the wheat flour mixture is not limited to a particular wheat cultivar and is, for example, Keumkang, Olgeuru, Jokyung, Jopoom, Baekjoong, or Goso.

In the method for producing a processed food, the dough described in the process (b) may be prepared according to a method known in the art, in which case, factors such as a moisture content, types and amounts of additives used, performance of aging, and aging time may be changed according to the characteristics of various processed food to be produced using the wheat flour.

In the method for producing a processed food, the processing of the dough described in the process (c) may be carried out by any method known in the art. For example, the dough is processed by a method of heat-treating the dough in a short time to produce a processed food such as cookies or biscuits, a method of preparing a sheet by stretching the dough and then drying the sheet to produce a processed food such as noodles, or a method of heat-treating the dough initially at mild temperature and then at high temperature to produce a processed food such as bread.

The processed food produced by the aforementioned method may be bread, noodles, cookies or the like, but is not limited to those listed as long as it can prevent the risks of gluten intolerance and WDEIA by reflecting the characteristics of the novel wheat cultivar of the present invention in which LMW-GS alleles located at the Glu-B3 loci and/or ω-5 gliadin genes have been deleted.

When a person inherently lacking a gluten-degrading enzyme ingests bread, the person generally suffers from gluten intolerance which is caused by undegraded gluten absorbed into the intestines without being broken down and may lead to celiac disease that impairs intestinal function, damages and weakens the villi in the mucous membrane and thereby causes malabsorption and eventually an allergic reaction, hormonal disturbance or the like. However, since LMW-GS alleles located at the Glu-B3 loci (major cause of gluten intolerance) have been deleted in the novel wheat cultivar provided in the present invention, a processed food produced using the wheat flour of the wheat cultivar as a main ingredient does not induce gluten intolerance even when ingested by a person inherently lacking a gluten-degrading enzyme, and thereby the onset of celiac disease can be prevented.

Ofree provided in the present invention is a wheat cultivar in which LMW-GS alleles located at the Glu-B3 loci (major cause of gluten intolerance) and/or ω-5 gliadin genes (cause of WDEIA) have been deleted; therefore, it can be widely used for the production of processed foods that can prevent the onset of celiac disease caused by gluten intolerance and/or the onset of WDEIA.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a genealogy diagram for illustrating the process of developing Ofree, a new wheat cultivar.

FIG. 2A is an electrophoresis image for showing the results of polymerase chain reaction (PCR) amplification of genes located at the Glu-B3 loci in Keumkang, Olgeuru and Ofree.

FIG. 2B is an electrophoresis image for showing HMW-GS- and LMW-GS-related proteins in Keumkang, Olgeuru and Ofree.

FIG. 2C is an electrophoresis image for showing LMW-GS-related proteins in various amounts of an Ofree extract.

FIG. 3 is an electrophoresis image for showing the results of detection of ω-5 gliadin proteins by sodium dodecyl sulfate polyacrylamide gel electrophoresis (SDS-PAGE) analysis of a gliadin fraction in Keumkang, Olgeuru and Ofree, wherein the first, second and third lanes represent Keumkang, Olgeuru and Ofree, respectively.

FIG. 4 is an electrophoresis image for showing the results of detection of ω-5 gliadin proteins by acid polyacrylamide gel electrophoresis (A-PAGE) analysis of the glutenin fraction in Keumkang, Olgeuru, and Ofree, wherein the first, second and third lanes represent Ofree, Keumkang and Olgeuru, respectively.

FIG. 5 shows the results of reversed-phase high-performance liquid chromatography (RP-HPLC) analysis of a gliadin fraction in Keumkang, Olgeuru and Ofree (top to bottom).

FIG. 6 shows the immunoblotting results of ω-5 gliadin-specific antibodies in Keumkang, Olgeuru and Ofree.

FIG. 7 shows the results of two-dimensional electrophoresis performed on all seed storage protein fractions in Keumkang, Olgeuru, Ofree (DH20) and Butte 86 followed by immunoblotting using the serum of a wheat-dependent exercise-induced anaphylaxis (WDEIA) patient; and the results of protein analysis by tandem mass spectrometry (MS/MS) superimposed on the immunoblotting results.

FIG. 8 is a set of images for showing Ofree (DH20), Keumkang and Olgeuru on their heading date (A) and the grains (B) and bread pieces (C) of Ofree (DH20), Keumkang, and Olgeuru.

DETAILED DESCRIPTION OF EXEMPLARY EMBODIMENTS

Hereinafter, the present invention will be described in greater detail with reference to examples. However, these examples are for illustrative purposes only and the scope of the present invention is not limited to these examples.

Example 1: Development of New Wheat Variety

A novel wheat cultivar having high cold resistance and desirable growth habit was developed by artificially crossing Keumkang and Olgeuru to obtain a progeny wheat plant F1. Haploid of F1 was cultivated at CIMMYT in Mexico and testing the productivity of F1 for four years in Iksan. The novel wheat cultivar was named "Ofree" (FIG. 1).

FIG. 1 is a genealogy diagram for illustrating the process of developing a new wheat cultivar Ofree.

Example 2: Genotype Identification of Ofree

Example 2-1. Confirmation of Deletion of Genes Located at Glu-B3 Loci

The genetic characteristics of Ofree developed by the processes described in Example 1 were determined in terms of the expression levels of genes at the Glu-1 loci components of high-molecular-weight glutenin subunits (HMW-GSs) in gluten and genes at the Glu-3 loci that is components of low-molecular-weight glutenin subunits (LMW-GSs) in gluten.

In brief, a genomic DNA extraction kit for plants (SolGent Co., Ltd., Korea) was used to extract genomic DNA from the young leaves of Keumkang, Olgeuru and Ofree. Subsequently, polymerase chain reaction (PCR) was carried out using the genomic DNA extracted earlier as a template and primers capable of detecting genes at the Glu-A1, Glu-B1, Glu-D1, Glu-A3, Glu-B3 or Glu-D3 loci (listed below) to determine which of the genes at the Glu-1 and Glu-3 loci were contained in the genetic composition of Ofree (Table 1).

```
Glu-A1ab F:
                                       (SEQ ID NO: 1)
5'-AAGACAAGGGGAGCAAGGT-3'

Glu-A1ab R:
                                       (SEQ ID NO: 2)
5'-GTGCTCCGCGCTAACATG-3'

Glu-A1c F:
                                       (SEQ ID NO: 3)
5'-ACGTTCCCCTACAGGTACTA-3'
```

-continued

Glu-A1C R:
(SEQ ID NO: 4)
5'-TATCACTGGCTAGCCGACAA-3'

Glu-B1bcf F:
(SEQ ID NO: 5)
5'-TTCTCTGCATCAGTCAGGA-3'

Glu-B1bcf R:
(SEQ ID NO: 6)
5'-AGAGAAGCTGTGTAATGCC-3'

Glu-D1d F:
(SEQ ID NO: 7)
5'-GCCTAGCAACCTTCACAATC-3'

Glu-D1d R:
(SEQ ID NO: 8)
5'-GAAACCTGCTGCGGACAAG-3'

Glu-D1adf F:
(SEQ ID NO: 9)
5'-TTTGGGGAATACCTGCACTACTAAAAAGGT-3'

Glu-D1adf F:
(SEQ ID NO: 10)
5'-AAAAGGTATTACCCAAGTGTAACTTGTCCG-3'

Glu-D1adf R:
(SEQ ID NO: 11)
5'-AATTGTCCTGGCTGCAGCTGCGA-3'

Glu-A3a F:
(SEQ ID NO: 12)
5'-AAACAGAATTATTAAAGCCGG-3'

Glu-A3b R:
(SEQ ID NO: 13)
5'-GGTTGTTGTTGTTGCAGCA-3'

Glu-A3b F:
(SEQ ID NO: 14)
5'-55CAGATGCAGCCAAACAA-3'

Glu-3Ab R:
(SEQ ID NO: 15)
5'-GCTGTGCTTGGATGATACTCTA-3'

Glu-A3ac F:
(SEQ ID NO: 16)
5'-AACAGAATTATTAAAGCCGG-3'

Glu-A3ac R:
(SEQ ID NO: 17)
5'-CTGTGCTTGGATGATACTCTA-3'

Glu-A3d F:
(SEQ ID NO: 18)
5'-TTCAGATGCAGCCAAACAA-3'

Glu-A3d R:
(SEQ ID NO: 19)
5'-TGGGGTTGGGAGACACATA-3'

Glu-A3e F:
(SEQ ID NO: 20)
5'-AAACAGAATTATTAAAGCCGG-3'

Glu-A3e R:
(SEQ ID NO: 21)
5'-GGCACAGACGAGGAAGGTT-3'

Glu-B3d F:
(SEQ ID NO: 22)
5'-CACCATGAAGACCTTCCTCA-3'

Glu-B3d R:
(SEQ ID NO: 23)
5'-GTTGTTGCAGTAGAACTGGA-3'

-continued

Glu-B3fg F:
(SEQ ID NO: 24)
5'-TATAGCTAGTGCAACCTACCAT-3'

Glu-B3fg R:
(SEQ ID NO: 25)
5'-CAACTACTCTGCCACAACG-3'

Glu-B3g F:
(SEQ ID NO: 26)
5'-CAAGAAATACTAGTTAACACTAGTC-3'

Glu-B3g R:
(SEQ ID NO: 27)
5'-GTTGGGGTTGGGAAACA-3'

Glu-B3h F:
(SEQ ID NO: 28)
5'-CCACCACAACAAACATTAA-3'

Glu-B3h R:
(SEQ ID NO: 29)
5'-GTGGTGGTTCTATACAACGA-3'

Glu-B3i F:
(SEQ ID NO: 30)
5'-TATAGCTAGTGCAACCTACCAT-3'

Glu-B3i R:
(SEQ ID NO: 31)
5'-TGGTTGTTGCGGTATAATTT-3'

Glu-D3ab F:
(SEQ ID NO: 32)
5'-TTGGGCCTAATCGCTCGC-3'

Glu-D3ab R:
(SEQ ID NO: 33)
5'-TAGTCTCCATCTGCGCAATT-3'

Glu-D3c F:
(SEQ ID NO: 34)
5'-CAGCTAAACCCATGCAAGC-3'

Glu-D3c R:
(SEQ ID NO: 35)
5'-CAATGGAAGTCATCACCTCAA-3'

TABLE 1

Genetic composition of Glu-1 and Glu-3

| Wheat cultivars | HMW-GS | | | LMW-GS | | |
|---|---|---|---|---|---|---|
| and wheat lines | Glu-A1 | Glu-B1 | Glu-D1 | Glu-A3 | Glu-B3 | Glu-D3 |
| Keumkang | b | b | d | c | h | a |
| Olgeuru | b | b | f | d | d | a |
| Ofree | b | b | f | c | | a |

As shown in Table 1, most of the genes expressed in one of Keumkang and Olgeuru were also expressed in Ofree, except for Glu-B3 (FIG. 2A).

FIG. 2A is an electrophoresis image for showing the results of polymerase chain reaction (PCR) amplification of genes located at the Glu-B3 loci in Keumkang, Olgeuru and Ofree. As shown in FIG. 2A, genes located at the Glu-B3 loci were not detected from Ofree.

Hence, for the purpose of detecting genes located at the Glu-B3 loci at the protein level, sodium dodecyl sulfate polyacrylamide gel electrophoresis (SDS-PAGE) of Keumkang, Olgeuru and Ofree extracts obtained from young leaves was carried out (FIG. 2B)

FIG. 2B is an electrophoresis image for showing HMW-GS- and LMW-GS-related proteins in Keumkang, Olgeuru and Ofree. As shown in FIG. 2B, no gene was detected at the Glu-B3 loci of Ofree even at the protein level.

In addition, to find out whether the results shown in FIG. 2B were obtained because of an insufficient amount of the Ofree extract used for SDS-PAGE, various amounts of the Ofree extract were subjected to SDS-PAGE (FIG. 2C).

FIG. 2C is an electrophoresis image for showing LMW-GS-related proteins in various amounts of the Ofree extract. As shown in FIG. 2C, as the amount of the Ofree extract increased, the amount of various proteins detected also increased accordingly except for genes located at the Glu-B3 loci, which were still not detected even when a large amount of the Ofree extract was examined.

To summarize the results shown in FIGS. 2A to 2C, since Ofree provided in the present invention is a wheat cultivar in which LMW-GS alleles located at the Glu-B3 loci (major cause of gluten intolerance) have been deleted, it can be used in the production of a bakery product that can be ingested by a person with gluten intolerance without causing side effects.

Example 2-2. Confirmation of Deletion of ω-5 Gliadin Genes in Ofree

Gliadin extraction was performed by consulting a prior-art document (Dziuba M, Nałęcz D, Szerszunowicz I, Waga J. 2014. Proteomic analysis of wheat α/A- and β-gliadins. Czech J Food Sci 32: 437-442). 1 ml of a 0.15 M aqueous NaCl solution was mixed with 100 mg of each of finely pulverized Keumkang, Olgeuru, and Ofree. Each mixture was reacted for two hours at 25° C., centrifuged at the speed of 15,000 rpm at 20° C. for five minutes, and then a supernatant thereof was removed. The precipitate was mixed with 1 ml of a 70% aqueous ethanol solution, the mixture was reacted for 12 hours at a constant temperature and centrifuged at the speed of 15,000 rpm at 20° C. for five minutes, and then a supernatant of the mixture was stored at 20° C.

Sodium Dodecyl Sulfate Polyacrylamide Gel Electrophoresis (SDS-PAGE) Analysis and Results A gliadin stored at −20° C. was mixed with a sample buffer (50 mM Tris-HCl, pH 6.8, 8% β-mercaptoethanol, 2% SDS, 20% glycerol) in a ratio of 1:2 to produce a mixture, and 5 μl of the mixture was loaded onto a 12.5% SDS-PAGE gel and subjected to electrophoresis at 70 V for 13 hours and at 110 V for four hours. After electrophoresis, the gel was stained with a Coomassie Brilliant Blue R-250 staining solution (Bio-Rad Laboratories, Inc.) for four hours and then decolorized with a decolorizing solution (10% glacial acetic acid, 10% methanol, 80% distilled water) for five hours, and the obtained protein band patterns were analyzed.

According to the results shown in FIG. 3, no ω-5 gliadin was detected from Ofree, unlike the cases of Keumkang and Olgeuru.

Acid Polyacrylamide Gel Electrophoresis (A-PAGE) Analysis and Results 1 ml of 70% ethanol was mixed with 100 mg of each of finely pulverized Keumkang, Olgeuru and Ofree. Each mixture was stirred at 25° C. for one hour, centrifuged at the speed of 14,000 rpm at a constant temperature for 10 minutes, and 500 μl of a supernatant thereof was mixed with 250 μl of a 5:1 solution of glycerin and 1% methyl violet.

10 μl of a gliadin was added to a 12% gel solution (12% acrylamide, 0.6% bis-acrylamide, 0.1% ascorbic acid, 0.004% Iron (II) sulfate heptahydrate, 0.25% aluminum lactate, pH adjusted to 3.1 with lactic acid), and the mixture was loaded and subjected to electrophoresis at 400 V for five hours. Then, the gel was stained with a Coomassie Brilliant Blue R-250 staining solution for three hours and then decolorized with 10% acetic acid and 10% methanol for four hours, and the obtained protein band patterns were analyzed.

According to the results shown in FIG. 4, no ω-5 gliadin was detected from Ofree-unlike the cases of Keumkang and Olgeuru.

Reversed-Phase High-Performance Liquid Chromatography (RP-HPLC) Analysis and Results 1 ml of 70% ethanol was mixed with 100 mg of each of finely pulverized Keumkang, Olgeuru and Ofree. Each mixture was reacted at 25° C. for one day, centrifuged at the speed of 15,000 rpm at 20° C. for five minutes, and then a supernatant thereof was dissolved with 300 ml of 0.1% trifluoroacetic acid (TFA) in 20% acetonitrile (ACN) and filtered with a Whatman polyvinylidene fluoride (PVDF) syringe filter (0.45 μm, Sigma-Aldrich Co. LLC). High-performance liquid chromatography (HPLC) was performed using an Agilent Zorbax 300SB-C18 column (300 Å pore size, 5 μm particle size, 4.6 mm inner diameter, 150 mm length) and a Waters Alliance e2695 HPLC system. Solvents used for HPLC include solvent A (0.1% TFA in water), solvent B (0.1% TFA in ceric ammonium nitrate (CAN)), solvent C (MeOH) and solvent D (MeOH). For analysis, 10 μl of each sample was injected and separations were accomplished with a linear gradient of 25 to 50% (solvent B) for 70 minutes and a flow rate of 1 ml/min, and a column temperature of 65° C. and a sample temperature of 15° C. were maintained. The analyzed samples were observed at 210 nm.

FIG. 5 shows the results of RP-HPLC analysis of a gliadin fraction in Keumkang, Olgeuru and Ofree. As shown in FIG. 5, no ω-5 gliadin was detected from Ofree unlike the cases of Keumkang and Olgeuru.

Results of Immunoblotting Using ω-5-Gliadin-Specific Antibodies

Total protein extraction, two-dimensional electrophoresis and immunoblotting were performed by referencing a document (Susan B. Altenbach et al. 2015. Assessment of the allergenic potential of transgenic wheat (Triticum aestivum) with reduced levels of ω5-gliadins, the major sensitizing allergen in wheat-dependent exercise-induced anaphylaxis. Journal of Agricultural and Food Chemistry. DOI: 10.1021). Total protein extraction from 100 mg of each of finely pulverized Keumkang, Olgeuru, and Ofree was performed using a 2% SDS sample buffer (2% SDS, 10% glycerol, 0.04 M Tris-HCl, pH 8.5, 50 mM DTT). Isoelectric focusing (IEF) was manually performed using an ampholyte (pI 3-10) and a capillary tube, and the second electrophoresis was performed on a NuPAGE™ 4-12% Bis-Tris protein gel. Proteins in two-dimensional gel electrophoresis (2-DE) spots were identified by tandem mass spectrometry (MS/MS). The MS/MS analysis was carried out by the method described in a document (Dupont, F M, Vensel W H, Tanaka C K, Hurkman II W J, Altenbach S B. 2011. Deciphering the complexities of the wheat flour proteome using quantitative two-dimensional electrophoresis, three proteases and tandem mass spectrometry. Proteome Science. 9(10). Available at: proteomesci.com). For each spot, three types of proteases (trypsin, chymotrypsin, thermolysin) were used to obtain maximum amino acid sequence coverage. The NCBI protein accession numbers obtained as a result of protein identification within each spot are provided in FIG. 6. ω-5 gliadin (BAE20328), i-type LMW-GS (AAS10189), s-type LMW-GS (BAD12055, AEI00677) and m-type LMW-GS (AEI00671) were identified from Keumkang, and ω-5 gliadins (BAE20328, AII26682), i-type LMW-GSs (AGM38903, ACY08811) and s-type LMW-GS (ACY08813) were identified from Olgeuru. After 2-DE, the total protein was transferred to a nitrocellulose membrane. The serum of the same patient was subjected to immunoblotting.

As shown in FIG. 6, no ω-5 gliadin protein was produced in Ofree.

Results of Immunoblotting Analysis Using Serum of WDEIA Patient

Total protein extraction, two-dimensional electrophoresis and immunoblotting were performed by referencing a document (Susan B. Altenbach et al. 2015. Assessment of the allergenic potential of transgenic wheat (*Triticum aestivum*) with reduced levels of ω5-gliadins, the major sensitizing allergen in wheat-dependent exercise-induced anaphylaxis. Journal of Agricultural and Food Chemistry. DOI: 10.1021). Total protein extraction from 100 mg of each of finely pulverized Keumkang, Olgeuru, and Ofree was performed using a 2% SDS sample buffer (2% SDS, 10% glycerol, 0.04 M Tris-HCl, pH 8.5, 50 mM DTT). Isoelectric focusing (IEF) was manually performed using an ampholyte (pI 3-10) and a capillary tube, and the second electrophoresis was performed on a NUPAGE™ 4-12% Bis-Tris protein gel. Proteins in 2-DE spots were identified by MS/MS. The MS/MS analysis was carried out by the method described in a document (Dupont F M, Vensel W H, Tanaka C K, Hurkman II W J, Altenbach S B. 2011. Deciphering the complexities of the wheat flour proteome using quantitative two-dimensional electrophoresis, three proteases and tandem mass spectrometry. Proteome Science. 9(10). Available at: proteomeci.com). For each spot, three types of proteases (trypsin, chymotrypsin, thermolysin) were used to obtain maximum amino acid sequence coverage. The NCBI protein accession numbers obtained as a result of protein identification within each spot are provided in FIG. 7. After 2-DE, the total protein was transferred to a nitrocellulose membrane. An antibody was prepared using RLLSPRGKELG (SEQ ID NO:36) which is a sequence specific to ω-5 gliadins and was used for immunoblotting.

All seed storage protein fractions in Keumkang, Olgeuru, Ofree (DH20) and Butte 86 were subjected to two-dimensional electrophoresis and immunoblotting was performed using the serum of a WDEIA patient. The results of protein analysis by MS/MS are provided, in a superimposed manner, along with the immunoblotting results of the WDEIA patient (FIG. 7). An ω-5 gliadin (BAE20328), i-type LMW-GS (AAS10189), s-type LMW-GSs (BAD12055, AEI00677) and m-type LMW-GS (AEI00671) were identified from Keumkang and ω-5 gliadins (BAE20328, A1126682), i-type LMW-GSs (AGM38903, ACY08811), s-type LMW-GSs (ACY08813, ACA63868, AEI00677) and m-type LMW-GSs (AGK83389, ACP27643) were identified from Olgeuru. On the other hand, as clearly seen in FIG. 7, no antigen-antibody reaction associated with ω-5 gliadins was observed in the WDEIA patent. Therefore, it was confirmed that Ofree (DH20) can reduce an allergic immune response leading to WDEIA.

Hence, the inventors of the present invention deposited Ofree with Korean Agricultural Culture Collection (KACC) of National Institute of Agricultural Sciences (166, Nong-saengmyeong-ro, Iseo-myeon, Wanju-gun, Jeollabuk-do. Republic of Korea) on Sep. 21, 2015, with the deposit number KACC88001BP.

Example 3: Characterization of Ofree

Various characteristics such as intrinsic characteristics, agricultural traits, yield characteristics, disease resistance, quality characteristics and baking-related characteristics of Ofree developed by the processes described in Example 1 were determined in accordance with Analysis Standards for Research in Agricultural Science and Technology (Rural Development Administration, 2012) and a guideline for characterization of crops in preparation for testing new varieties were provided by the National Seed Management Office of Ministry of Agriculture and Forestry, and the obtained results were compared to the characteristics of Keumkang and Olgeuru, the parent wheat plants.

Example 3-1. Intrinsic Characteristics

The intrinsic characteristics of Ofree in terms of seeding establishment, cold resistance, growth level, leaf color, growth habit, branches and leaves, and uniformity were determined (Table 2).

TABLE 2

Intrinsic characteristics of Ofree

| Wheat cultivars and wheat lines | Seeding establishment | Cold resistance | Growth | Leaf color | Growth habit | Branches and leaves | Uniformity |
| --- | --- | --- | --- | --- | --- | --- | --- |
| Keumkang | Good | 3 | Good | Light green | Semi-erect | Slightly drooping | Good |
| Olgeuru | Good | 3 | Good | Yellow-green | Semi-open | Slightly drooping | Good |
| Ofree | Good | 3 | Good | Yellow-green | Semi-erect | Slightly drooping | Good |

As shown in Table 2, Ofree had generally similar intrinsic characteristics to those of Keumkang and Olgeuru, except for the leaf color which was similar to that of Olgeuru and the growth habit, which was similar to that of Keumkang.

Example 3-2. Agricultural Traits

The agricultural traits of Ofree in terms of heading date, maturing date, stem length and panicle length were determined (Table 3).

TABLE 3

Agricultural traits of Ofree

| Wheat cultivars and wheat lines | Heading date | Maturing date | Stem length (cm) | Panicle length (cm) |
| --- | --- | --- | --- | --- |
| Keumkang | May 4th | June 11th | 69 | 9.4 |
| Olgeuru | May 6th | June 13th | 66 | 8.6 |
| Ofree | May 9th | June 12th | 66 | 9.2 |

As shown in Table 3, the heading date and maturing date of Ofree were generally similar to those of Keumkang and Olgeuru, and the stem length of Ofree was the same as that of Olgeuru, and the panicle length of Ofree was similar to that of Keumkang.

Example 3-3. Yield Characteristics

The yield characteristics of Ofree in terms of the number of spikes per area, number of grains per spike, thousand-grain-weight, grain weight per liter, and yield per area were determined (Table 4).

TABLE 4

Yield characteristics of Ofree

| Wheat cultivars and wheat lines | Number of spikes per area (/m²) | Number of grains per spike | Thousand-grain-weight (g) | Grain weight per liter (g) | Yield per area (kg/10a) |
|---|---|---|---|---|---|
| Keumkang | 1,041 | 35 | 42.4 | 806 | 422 |
| Olgeuru | 880 | 37 | 41.5 | 815 | 485 |
| Ofree | 622 | 36 | 47.5 | 810 | 386 |

As shown in Table 4, Ofree had a similar number of grains per spike but a significantly lower number of spikes per area compared to Keumkang or Olgeuru, and thus a significantly lower yield per area compared to Keumkang or Olgeuru. However, Ofree had a more desirable yield quality compared to Keumkang or Olgeuru in some aspects by having a larger thousand-grain-weight compared to Keumkang or Olgeuru and an intermediate grain weight per liter between Keumkang and Olgeuru.

Example 3-4. Disease Resistance

To evaluate the disease resistance of Ofree, the resistance of Ofree to *Fusarium* head blight, virus infection, wheat flour mildew and sheath eyespot was examined (Table 5).

TABLE 5

Disease resistance of Ofree

| Wheat cultivars and wheat lines | *Fusarium* head blight (high, medium, low) | Virus infection (high, medium, low) | Flour mildew (high, medium, low) | Sheath eyespot (affected, not affected) |
|---|---|---|---|---|
| Keumkang | Medium-low | Medium | Medium-high | Not affected |
| Olgeuru | Low | Medium-high | Medium-high | Not affected |
| Ofree | Low | Medium-high | Medium-high | Not affected |

As shown in Table 5, Ofree had the same level of disease resistance as Olgeuru.

Example 3-5. Baking-Related Characteristics

The baking-related characteristics of Ofree in terms of flour milling characteristics, dough characteristics, and baking characteristics were determined.

Example 3-5-1. Flour Milling Characteristics

The harvested Ofree was milled into flour in a Buhler mill and the flour milling percentage, ash content and flour color of the wheat flour were determined after one month of flour aging (Table 6). In this case, the ash content in the flour was measured in accordance with AACC Method 08-01 (AACC International 2000), and the flour color in terms of whiteness, redness and yellowness was measured with Minolta JS-555 (Konica Minolta, Inc., Japan) and the flour color results were expressed in terms of CIELAB L* (whiteness) a* (redness), and b* (yellowness) axes.

TABLE 6

Flour milling characteristics of Ofree

| Wheat cultivars and wheat lines | Flour milling percentage (%) | Ash (%) | Flour color L | Flour color a | Flour color b |
|---|---|---|---|---|---|
| Keumkang | 72.57 | 0.46 | 91.62 | 2.10 | 9.21 |
| Olgeuru | 67.19 | 0.40 | 92.65 | 1.53 | 7.89 |
| Ofree | 71.50 | 0.44 | 91.55 | 2.00 | 8.72 |

As shown in Table 6, the flour made from Ofree (i.e. Ofree flour) had flour milling percentage, ash content and flour color that are roughly intermediate between those of the Keumkang flour and Olgeuru flour but more similar to those of the Keumkang flour than to those of the Olgeuru flour. The L value of Ofree was lower than that of Keumkang or Olgeuru.

Example 3-5-2. Dough Characteristics

The total protein content, gluten content, and sedimentation value of the Ofree flour produced according to Example 3-5-1 were measured and the characteristics of a dough made of the Ofree flour in terms of an amount of water added, kneading time, and dough stability were measured (Table 7). In this case, the total protein content and gluten content were measured in accordance with AACC Method 46-30 (AACC International 2000); the sedimentation value was determined by the processes of placing 3 g of the flour (based on 14% moisture content) in a 100 ml cylinder, adding 50 ml of a 0.0004% bromophenol blue solution into the cylinder, shaking the cylinder for 15 seconds twice with a two-minute interval, adding 50 ml of a 2% SDS solution containing 12.5% lactic acid into the cylinder and shaking the cylinder for 15 seconds three times with a two-minute interval, leaving the cylinder for 20 minutes, and then measuring the level of the precipitate; and the dough characteristics were determined using a 10 g mixograph (National Mfg. Co., United States) in accordance with AACC Method 54-40A (AACC International 2000).

TABLE 7

Dough characteristics of Ofree

| Wheat cultivars and wheat lines | Protein (%) | Gluten (%) | Sedimentation value (ml) | Water added (%) | Kneading time (min:sec) | Stability (mm) |
|---|---|---|---|---|---|---|
| Keumkang | 15.66 | 15.15 | 70.00 | 67.00 | 4:00 | 18.00 |
| Olgeuru | 12.35 | 10.95 | 48.50 | 63.00 | 2:30 | 13.00 |
| Ofree | 14.78 | 13.60 | 66.00 | 67.00 | 3:15 | 16.00 |

As shown in Table 7, the Ofree flour had a protein content, gluten content, sedimentation value and dough characteristics that are roughly intermediate between those of the Keumkang flour and Olgeuru flour but more similar to those of the Keumkang flour than to those of the Olgeuru flour. The Ofree flour had the characteristics of strong wheat flour by requiring the same amount of water to be added to make a dough as the Keumkang flour and, at the same time, characteristics similar to those of medium wheat flour in terms of the kneading time.

Example 3-5-3. Baking Characteristics

Bread was baked using the Ofree flour produced according to Example 3-5-1, and the bread loaf volume and crumb firmness, which are representative of bread characteristics, of the obtained bread were determined (Table 8). In this case, the bread loaf volume was measured using a loaf volumeter (National Mfg. Co., United States) immediately after baking in the oven, and the crumb firmness was determined by cooling the bread at room temperature for two hours, cutting out a crumb with a thickness of 2.0 cm from the central part of the bread loaf, and using a Texture Analyser with a 2.5 cm-diameter plastic plunger at a rate of 1.0 mm/sec at 25% strain with respect to the crumb thickness.

TABLE 8

Baking characteristics of Ofree

| Wheat cultivars and wheat lines | Bread loaf volume (ml) | Crumb firmness (N) |
|---|---|---|
| Keumkang | 900 | 2.60 |
| Olgeuru | 692 | 5.04 |
| Ofree | 793 | 2.53 |

As shown in Table 8, the bread produced using the Ofree flour (i.e. Ofree bread) was rated as having a larger volume and greater softness compared to the Olgeuru bread by having a bread loaf volume and crumb firmness that are intermediate between those of Keumkang bread and Olgeuru bread.

FIG. 8 is a set of images for showing Ofree (DH20), Keumkang, and Olgeuru on their heading date (A), and the grains (B) and bread pieces (C) of Ofree (DH20), Keumkang, and Olgeuru.

Production Example: Production of Cookies Using Flour Obtained from Ofree

Ofree cookies were produced in the following manner.

150 g of butter was gently beaten in a mixer to loosen the butter, 100 g of sugar was added into the mixer, and the contents were homogenized with a whisk for creaming. Then, 120 g of egg was added into the mixer and blended to form a mixture, and mixed wheat flour (100 g of Ofree flour and 300 g of typical soft wheat flour), 30 g of almond powder, 24 g of cocoa were gently blended with the mixture to prepare a base dough.

50 g of milk was added little by little to the base dough to adjust the consistency of the dough and 20 g of whipped cream was added to the dough, which was then rolled uniformly to a 1 cm thickness and stored in a freezer. In the freezer, egg white and sugar were applied to the surface of the frozen dough, which was then cut into pieces with a size of 1 cm (width)×10 cm (length). The pieces were arranged on a baking tray and then baked in a preheated oven for 15 minutes with a top-heat temperature of 190° C. and a bottom-heat temperature of 165° C. to produce Ofree cookies. The baked cookies were cooled at room temperature for about four hours.

It will be understood by those skilled in the art that various changes or modifications may be made to the present invention without departing from the spirit and scope of the present invention as defined by the appended claims.

[Deposition Number]

Depositary name: Korean Agricultural Culture Collection (KACC)

Deposition number: KACC88001BP

Deposited on: Sep. 21, 2015

What is claimed is:

1. A new wheat cultivar in which low-molecular-weight glutenin subunit (LMW-GS) alleles located at Glu-B3 loci have been deleted, the new wheat cultivar is deposited with a deposition number KACC88001BP.

2. A method of developing an improved wheat cultivar, the method including using the new wheat cultivar according to claim 1 as a father plant or a mother plant for crossing with another wheat cultivar.

3. The method of claim 2, wherein the other wheat cultivar is Jokyung wheat, Jopoom wheat, Baekjoong wheat, or Goso wheat.

4. Wheat flour obtained by milling the new wheat cultivar according to claim 1.

5. A food composition including the wheat flour according to claim 4.

6. The food composition according to claim 5, wherein the food composition is noodles, cookies, or bread.

7. A method of producing a processed food, the method including:
   (a) obtaining wheat flour by milling the new wheat cultivar according to claim 1;
   (b) preparing a dough containing the wheat flour; and
   (c) processing the dough.

8. The method according to claim 7, further comprising: mixing the wheat flour obtained from (a) with wheat flour obtained from another wheat cultivar to form mixed flour.

9. The method according to claim 8, wherein the wheat flour obtained from (a) is included in the mixed flour in an amount of 50 to 99% v/v.

10. The method according to claim 8, wherein the another wheat cultivar is selected from the group consisting of Keumkang wheat, Olgeuru wheat, Jokyung wheat, Jopoom wheat, Baekjoong wheat, Goso wheat, and combinations thereof.

* * * * *

SEQUENCE LISTING

<160> NUMBER OF SEQ ID NOS: 36

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
aagacaaggg gagcaaggt                                              19

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
gtgctccgcg ctaacatg                                               18

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
acgttcccct acaggtacta                                             20

```
<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tatcactggc tagccgacaa                                                 20

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
ttctctgcat cagtcagga                                                  19

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
agagaagctg tgtaatgcc                                                  19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gcctagcaac cttcacaatc                                                 20

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
gaaacctgct gcggacaag                                                  19

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
tttggggaat acctgcacta ctaaaaaggt                                      30

<210> SEQ ID NO 10
<211> LENGTH: 30
<212> TYPE: DNA
<213> ORGANISM: Artificial Sequence
<220> FEATURE:
<223> OTHER INFORMATION: primer
```

```
<400> SEQUENCE: 10
aaaaggtatt acccaagtgt aacttgtccg                                    30

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
aattgtcctg gctgcagctg cga                                           23

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
aaacagaatt attaaagccg g                                             21

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
ggttgttgtt gttgcagca                                                19

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
ttcagatgca gccaaacaa                                                19

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
gctgtgcttg gatgatactc ta                                            22

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
aacagaatta ttaaagccgg                                               20

<210> SEQ ID NO 17
```

```
<211> LENGTH: 21
<212> TYPE: DNA
<213> ORGANISM: Artificial Sequence
<220> FEATURE:
<223> OTHER INFORMATION: primer

<400> SEQUENCE: 17
ctgtgcttgg atgatactct a                                               21

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
ttcagatgca gccaaacaa                                                  19

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
tggggttggg agacacata                                                  19

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
aaacagaatt attaaagccg g                                               21

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
ggcacagacg aggaaggtt                                                  19

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
caccatgaag accttcctca                                                 20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
```

```
gttgttgcag tagaactgga                                                      20

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
tatagctagt gcaacctacc at                                                   22

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
caactactct gccacaacg                                                       19

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
caagaaatac tagttaacac tagtc                                                25

<210> SEQ ID NO 27
<211> LENGTH: 17
<212> TYPE: DNA
<213> ORGANISM: Artificial Sequence
<220> FEATURE:
<223> OTHER INFORMATION: primer

<400> SEQUENCE: 27
gttggggttg ggaaaca                                                         17

<210> SEQ ID NO 28
<211> LENGTH: 19
<212> TYPE: DNA
<213> ORGANISM: Artificial Sequence
<220> FEATURE:
<223> OTHER INFORMATION: primer

<400> SEQUENCE: 28
ccaccacaac aaacattaa                                                       19

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
gtggtggttc tatacaacga                                                      20

<210> SEQ ID NO 30
<211> LENGTH: 22
<212> TYPE: DNA
```

```
<213> ORGANISM: Artificial Sequence
<220> FEATURE:
<223> OTHER INFORMATION: primer

<400> SEQUENCE: 30
tatagctagt gcaacctacc at                                              22

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
tggttgttgc ggtataattt                                                 20

<210> SEQ ID NO 32
<211> LENGTH: 18
<212> TYPE: DNA
<213> ORGANISM: Artificial Sequence
<220> FEATURE:
<223> OTHER INFORMATION: primer

<400> SEQUENCE: 32
ttgggcctaa tcgctcgc                                                   18

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
tagtctccat ctgcgcaatt                                                 20

<210> SEQ ID NO 34
<211> LENGTH: 19
<212> TYPE: DNA
<213> ORGANISM: Artificial Sequence
<220> FEATURE:
<223> OTHER INFORMATION: primer

<400> SEQUENCE: 34
cagctaaacc catgcaagc                                                  19

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
caatggaagt catcacctca a                                               21

<210> SEQ ID NO 36
<211> LENGTH: 11
```

```
<212> TYPE: PRT
<213> ORGANISM: Artificial Sequence
<220> FEATURE:
<223> OTHER INFORMATION: a sequence specific to omega-5 gliadins

<400> SEQUENCE: 36

Arg Leu Leu Ser Pro Arg Gly Lys Glu Leu Gly
1               5                   10
```